United States Patent
Maruyama et al.

(12) 
(10) Patent No.: US 6,387,667 B1
(45) Date of Patent: May 14, 2002

(54) PROCESS FOR PRODUCING CYTIDINE DIPHOSPHATE CHOLINE

(75) Inventors: Akihiko Maruyama, Machida; Tatsuro Fujio, Hofu; Sadao Teshiba, Machida, all of (JP)

(73) Assignee: Kyowa Hakko Kogyo, Co., Ltd., Tokyo (JP)

( * ) Notice: Subject to any disclaimer, the term of this patent is extended or adjusted under 35 U.S.C. 154(b) by 0 days.

(21) Appl. No.: 08/014,012

(22) Filed: Jan. 28, 1993

(30) Foreign Application Priority Data

Jan. 30, 1992 (JP) ............................................. 4-014858

(51) Int. Cl.$^7$ ........................... C12P 17/12; C12P 13/00
(52) U.S. Cl. ....................................... 435/122; 435/128
(58) Field of Search ................................ 435/122, 128, 435/172.3

(56) References Cited

U.S. PATENT DOCUMENTS

RE28,886 E * 6/1976 Nakayama et al. ............ 435/89
4,789,666 A * 12/1988 Gennari ........................ 514/51

FOREIGN PATENT DOCUMENTS

| DE | 2054785 | 6/1971 |
| GB | 1294769 | 11/1972 |
| JP | 63-313594 | 12/1988 |

OTHER PUBLICATIONS

American Type Culture Collection Catalog of Bacteria and Phages, 18$^{th}$ Edition, 1992, American Type Culture Collection, Rockville, MD.*

Ozier–Kalogeropoulos, O. et al.; Mol. Gen. Genet. 231:7–16 (1991).*

Tsukagoshi, Y. et al.; J. Bacteriol. 173:2134–2136 (1991).*

Hosaka, K. et al.; J. Biol. Chem. 264:2053–2059 (1989).*

Weng, M. et al.; J. Biol. Chem. 261: 5568–5574 (1986).*

Nudler, A.A. et al.; FEMS Microbiol. Lett. 82:263–266 (1991).*

Neuhard, J. et al.; In Neidhardt, F.C et al. (EDS.) *Escherichia coli* and *Salmonella typhimurium*—Cellular and Molecular Biology, American Soc. For Microbiology, Washington, D.C. (1987), pp. 445–473.*

Sigma Chemical Company, 1992 Catalog; Sigma Chemicals, St. Louis, MO, 1992, pp. 255, 302, 746–747, 811, 1009, 1011, 1012.*

* cited by examiner

*Primary Examiner*—Ponnathapu Achutamurthy
*Assistant Examiner*—Peter P. Tung
(74) *Attorney, Agent, or Firm*—Antonelli, Terry, Stout & Kraus, LLP

(57) ABSTRACT

A process for producing cytidine diphosphate choline is provided. The process comprises carrying out an enzymatic reaction using microorganisms having the enzyme activities of cytidine-5'-triphosphate synthetase (pyrG), cholinephosphate cytidylyltransferase (CCT) and choline kinase (CKI) and a microorganism capable of producing uridine-5'-triphosphate from orotic acid as the enzyme sources, and orotic acid and choline and/or phosphorylcholine as the substrates; allowing cytidine diphosphate choline to accumulate in the reaction mixture; and recovering cytidine diphosphate choline from said reaction mixture.

9 Claims, 3 Drawing Sheets

P: PstI, Hp: HpaI, H: HindIII,
K: KpnI, S: SmaI, Pv: PvuII,
M: MluI, N: NruI,
$P_{lac}$: lac promoter, Ap: Ampicillin

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 54 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
      (A) ORGANISM: Saccharomyc es cerevisiae
      (B) STRAIN: X2180-1

(xi) SEQUENCE DESCRIPTION: SEQ ID NO:1:

ATGACCATGA TTACGAATTC GAGCTCGGTA CCCAAAAAAA ATAAAAATAA A AGA     54

(2) INFORMATION FOR SEQ ID NO:2:

(i) SEQUENCE CHARACTERISTICS:
      (A) LENGTH: 18 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

Met Thr Met Ile Thr Asn Ser Ser Ser Val P ro Lys Lys Asn Lys
1         5                  10               15

Asn Lys Arg (2) INFORMATION FOR SEQ ID NO:3:

(i) SEQUENCE CHARACTERISTICS:
      (A) LENGTH: 18 base pairs
      (B) TYPE: nucleic acid

```
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (xi) SEQUENCE DESCRIPTION: SEQ ID NO:3:

ATGACTAAAA ATAAAAGA                                                18

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:4:

Met Thr Lys Asn Lys Arg
1               5
```

PROCESS FOR PRODUCING CYTIDINE DIPHOSPHATE CHOLINE

BACKGROUND OF THE INVENTION

The present invention relates to an enzymatic process for producing cytidine diphosphate choline (hereinafter referred to as CDP-choline) which is useful as a medicine.

CDP-choline is a biosynthetic intermediate for phosphatidyl choline (lecithin), which is a phospholipid, and is useful for the treatment of head injuries, disturbance of consciousness following cerebral surgery, Parkinson's disease, postapoplectic hemiplegia, etc.

Two kinds of processes are known for producing CDP-choline: chemical synthetic processes disclosed in Japanese Published Examined Patent Applications Nos. 6541/64, 1384/67, 6558/88, etc.; and enzymatic processes utilizing cells of microorganisms such as yeast disclosed in Japanese Published Examined Patent Applications Nos. 2358/73, 40757/73 and 40758/73 and Japanese Published Unexamined Patent Applications Nos. 109996/78, 14593/79 and 313594/88.

A feature common to these known processes is the use of cytosine nucleotides such as cytidine-5'-monophosphate (hereinafter referred to as CMP), cytidine-5'-diphosphate (hereinafter referred to as CDP), cytidine-5'-triphosphate (hereinafter referred to as CTP), and cytosine, or their precursors as starting materials.

Of these starting materials, the basic starting material, CMP, is mainly produced by the RNA (ribonucleic acid) decomposition method which provides four types of nucleotides at the same time. This method is inefficient in that it is impossible to selectively obtain CMP.

SUMMARY OF THE INVENTION

The present invention provides a process for producing CDP-choline, which comprises carrying out an enzymatic reaction using cultures of microorganisms having enzyme activities responsible for the production of CDP-choline from orotic acid and choline and/or phosphorylcholine or treatment products of the cultures as the enzyme sources and orotic acid and choline and/or phosphorylcholine as the substrates, allowing CDP-choline to accumulate in the reaction mixture, and recovering CDP-choline from said reaction mixture.

According to the present invention, CDP-choline can be produced with a high efficiency by enzymatic treatment from orotic acid which is easily available from industrial sources, not from a cytosine nucleotide or its precursor.

Orotic acid is a precursor of pyrimidine nucleotides which is used as a hepatotonic. An industrially applicable process is known for producing orotic acid by fermentation of microorganisms belonging to the genus Corynebacterium (EP-A-0312912). As a result of studies to develop a process for producing CDP-choline using orotic acid as a starting material, it has been found that CDP-choline can be produced in a high yield by enzymatic reaction in which a microorganism carrying a recombinant DNA prepared by incorporating into a vector DNA a DNA fragment containing genes coding for CTP synthetase (hereinafter referred to as pyrG), cholinephosphate cytidylyltransferase (hereinafter referred to as CCT) and choline kinase (hereinafter referred to as CKI) and a microorganism which has a high activity of producing uridine-5'-triphosphate (hereinafter referred to as UTP) from orotic acid are used in combination as enzyme sources, and orotic acid and choline and/or phosphorylcholine are used as substrates.

DETAILED DESCRIPTION OF THE INVENTION

Figure 1:
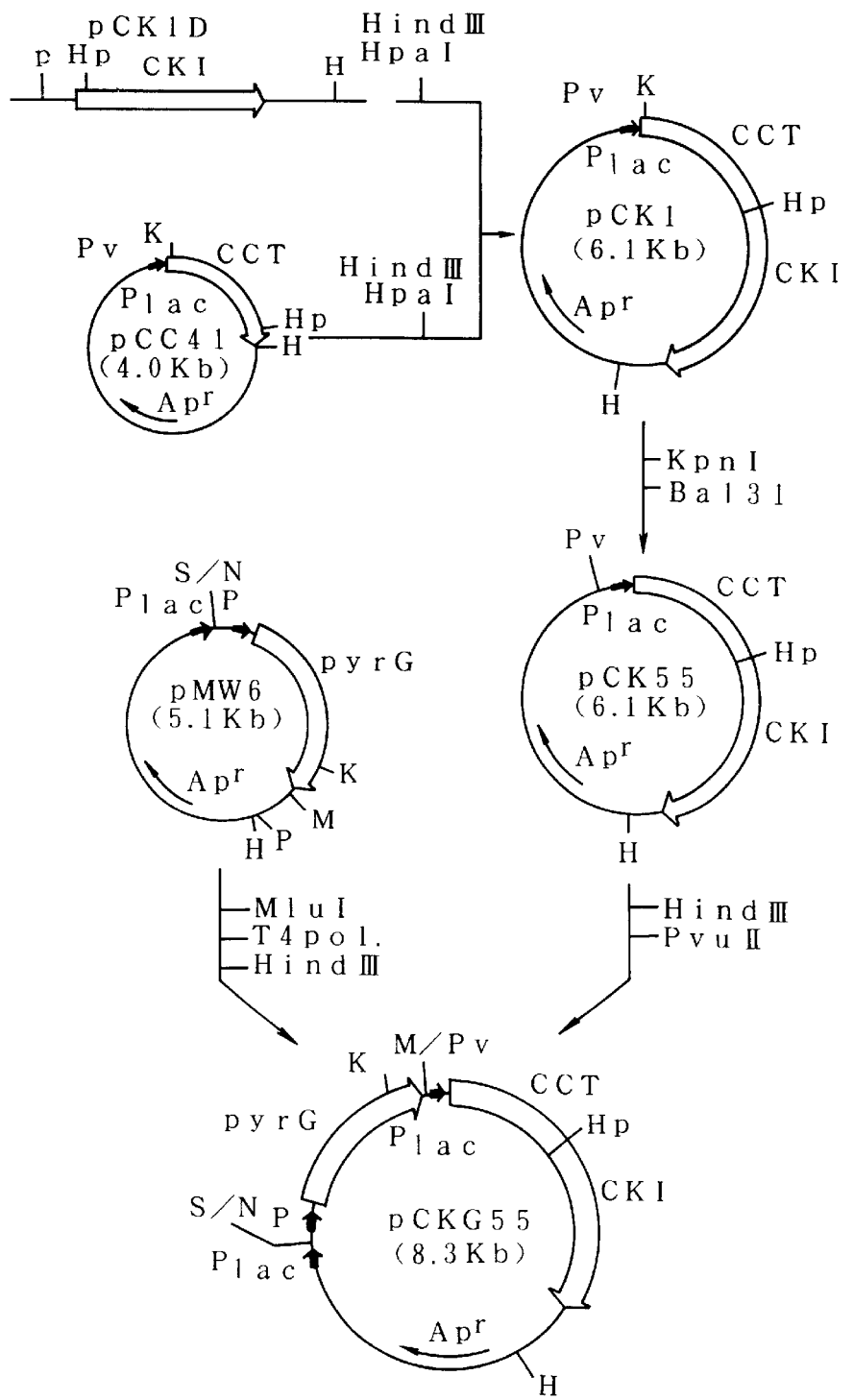
FIG. 1 shows a process for the construction of plasmid pCKG55.

In accordance with the present invention, enzymatic reaction is carried out using cultures of microorganisms having enzyme activities responsible for the production of CDP-choline from orotic acid and choline and/or phosphorylcholine or treated products of the cultures as the enzyme sources, and orotic acid and choline and/or phosphorylcholine as the substrates, whereby CDP-choline is accumulated in the reaction mixture.

In cases where orotic acid and phosphorylcholine are used as the substrates, CDP-choline can be produced by a 6-step enzymatic reaction from (1) to (6) as represented by the scheme given below. In cases where orotic acid and choline are used as the substrates, the additional step (7) is required.

The abbreviations used in the scheme stand for the following:

OMP: Orotidine-5'-monophosphate
UMP: Uridine-5'-monophosphate
UDP: Uridine-5'-diphosphate
UTP: Uridine-5'-triphosphate The enzymes which catalyze the reactions of the steps (1) through (7) are listed below.

(1) Orotate phosphoribosyltransferase (EC 2.4.2.10)
(2) OMP decarboxylase (EC 4.1.1.23)
(3) Nucleosidemonophosphate kinase (EC 2.7.4.4)
(4) Nucleosidediphosphate kinase (EC 2.7.4.6)
(5) CTP synthetase (EC 6.3.4.2)
(6) Cholinephosphate cytidylyltransferase (EC 2.7.7.15)
(7) Choline kinase (EC 2.7.1.32)

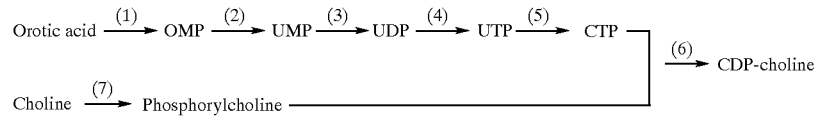

material, it has been found that CDP-choline can be produced in a high yield by enzymatic reaction in which a In the reaction of the above step (1), phosphoribosyl pyrophosphate (hereinafter referred to as PRPP) is consumed and pyrophosphoric acid is formed, and in the reactions of the above steps (3), (4), (5) and (7), adenosine-5'-triphosphate (hereinafter referred to as ATP) is consumed and adenosine-5'-diphosphate (hereinafter referred to as ADP) is formed.

Therefore, it is preferred to use microorganisms which have the enzyme activities of (1)–(7) mentioned above, and further the activities of supplying PRPP and regenerating ATP. The number of microorganisms used is not limited so far as the above requirements are satisfied.

For example, as described below, it is possible to use a mixture of two kinds of microorganisms, one having some of the required activities and the other having the remaining activities. More particularly, it is possible to use a mixture of: (i) a microorganism having the enzyme activities of (5), (6) and (7) (hereinafter referred to as Microorganism A1) or a microorganism having the enzyme activities of (5) and (6) (hereinafter referred to as Microorganism A2) (Microorganisms A1 and A2 are sometimes collectively referred to as Microorganism A hereinafter); and (ii) a microorganism having the sufficient enzyme activities of (1) through (4) to form UTP from orotic acid and preferably further having the high activities of supplying PRPP and regenerating ATP (hereinafter referred to as Microorganism B).

As Microorganism A1 or A2, strains belonging to the genus Escherichia whose enzymatic activities are enhanced by recombinant DNA technology are preferably used. An example of such preferred strain is a transformant obtained by introducing a recombinant DNA pCKG55 containing the CCT and CKI genes derived from *Saccharomyces cerevisiae* (hereinafter referred to as yeast) and the pyrG gene derived from *Escherichia coli* (hereinafter referred to as *E. coli*) into *E. coli* MM294 strain (FPRM BP-526, ATCC 33625).

The CCT gene is cloned from the yeast chromosome making use of the complementation of yeast CCT gene deficiency mutation as an index, and its entire nucleotide sequence has been determined (Eur. J. Biochem., 169, 477–486, 1987). An example of the CCT gene source is plasmid pCC41 (Biochemistry, 60, 701, 1988) constructed by inserting a Dra I fragment of 1,296 base pairs (hereinafter referred to as bp) which contains the CCT gene derived from the yeast into *E. coli* vector pUC18 (Gene, 33, 103–119, 1985) at Sma I site of the multi-cloning sites.

The CKI gene is similarly cloned from the yeast chromosome, and its entire nucleotide sequence has also been determined (J. Biol. Chem., 264, 2053–2059, 1989). An example of the CKI gene source is plasmid pCK1D constructed by inserting a Pst I-Hind III fragment of 2,692 bp which contains the CKI gene derived from the yeast into shuttle vector YEpM4 for the yeast and *E. coli* (Mol. Cell. Biol., 7, 3629–3636, 1987).

The pyrG gene is cloned from the *E. coli* chromosome, and its entire nucleotide sequence has been determined (J. Biol. Chem., 261, 5568–5574, 1986). An example of the pyrG gene source is plasmid pMW6 constructed by inserting a Nru I-Pst I fragment of 2,426 bp which contains the pyrG gene derived from *E. coli* into *E. coli* vector pUC8 (Gene, 19, 259–268, 1982) at the Sma I-Pst I site of multi-cloning sites.

Isolation of the plasmid DNAs from *E. coli* strains carrying them may be carried out according to a known method (Nuc. Acids Res., 7, 1513–1523, 1979). Cleavage of the plasmid DNAs with restriction enzymes, isolation of DNA fragments formed by the cleavage, enzymatic ligation of the DNA fragments, transformation of a host *E. coli* strain with a recombinant DNA, and other various procedures for genetic recombination may be carried out by known methods (e.g., T. Maniatis et al., "Molecular Cloning, A Laboratory Manual," Cold Spring Harbor Laboratory, 1982).

Any vector can be used so far as it is capable of replication in a host microorganism. For example, when *E. coli* is used as the host, pUC8, pBR322 (Gene, 2, 95–113, 1977), etc. may be used.

Any microorganism can be used as the host so far as an introduced recombinant DNA can be expressed in it and it can be used in a reaction for the production of CDP-choline. For example, *E. coli* MM294 strain mentioned above may be used.

As Microorganism B, strains belonging to the genus Corynebacterium are preferably used. An example of preferred strain is *Corynebacterium ammoniagenes* (old designation: *Brevibacterium ammoniagenes*) ATCC 21170.

As the medium for culturing Microorganisms A1, A2 and B, any of natural media and synthetic media can be used, so far as they appropriately contain carbon sources, nitrogen sources, inorganic matters, amino acids, vitamins, etc. which can be assimilated by the microorganisms used. The microorganisms may be cultured in a conventional manner at a controlled temperature and pH under aerobic conditions.

As the carbon sources, carbohydrates such as glucose, fructose, sucrose, maltose, mannitol and sorbitol, sugar alcohols, glycerol, starch hydrolysate, molasses, various organic acids such as pyruvic acid, lactic acid and citric acid, and amino acids such as glutamic acid, methionine and lysine can be used. Natural organic nutrient sources such as bran, cassava, bagasse and corn steep liquor can also be used.

As the nitrogen sources, ammonia, various inorganic and organic ammonium salts such as ammonium chloride, ammonium sulfate, ammonium carbonate and ammonium acetate, amino acids such as glutamic acid, glutamine and methionine, and nitrogen-containing organic materials such as peptone, NZ amine, corn steep liquor, meat extract, yeast extract, casein hydrolysate, fish meal or its digest, and chrysalis hydrolysate can be used.

Further, if necessary, potassium dihydrogen phosphate, disodium hydrogenphosphate, magnesium sulfate, sodium chloride, calcium chloride, iron chloride, copper sulfate, manganese chloride, ammonium molybdate, zinc sulfate, and other inorganic matters may be added. Vitamins, amino acids, nucleic acids, etc. may also be added, but it is not necessary to add them if they are supplied by the other components of the medium mentioned above.

Culturing is carried out under aerobic conditions, for example, by shaking culture or aeration-agitation culture. Culturing temperature is usually in the range of 15° C. to 40° C., preferably 20° C. to 35° C. It is preferred to keep the pH of the medium around neutrality during the culturing. Culturing time is usually 5 to 72 hours.

Microorganism A which is capable of producing CDP-choline from UTP and choline and/or phosphorylcholine and Microorganism B which is capable of producing UTP from orotic acid may be cultured separately, and mixed after the completion of the culturing. Alternatively, they may be inoculated in the same fermentor simultaneously and subjected to mixed culture. Further, one of the microorganisms may be cultured first and the other may be added during the culturing or after the completion of the culturing.

The thus obtained cultures of Microorganisms A and B are subjected to the reaction for CDP-choline production, as such or after being treated in various manners. For the reaction, the mixed culture of Microorganisms A and B or its treated product may be brought into contact with orotic acid and choline and/or phosphorylcholine. Alternatively, the culture of Microorganism B or its treated product may be brought into contact with orotic acid to produce UTP, and then the culture of Microorganism A or its treated product may be added together with choline and/or phosphorylcholine.

The treated products of the culture include concentrates and dried products thereof, cells recovered from the culture by centrifugation, dried cells, surfactant and/or organic solvent-treated products, lytic enzyme-treated products, immobilized cells, and preparations of enzymes extracted from the cells.

To a mixture of the culture or its treated product and the substrates are further added substances required for the reaction for the production of CDP-choline, and the reaction is carried out at pH 6 to 10, preferably 7 to 8 at a temperature of 20° C. to 50° C. for 2 to 48 hours. Examples of the substances required for the reaction include energy donors necessary for the regeneration of ATP, phosphate ions, magnesium ions, ammonium ions, surfactants, and organic solvents. It is not necessary to add these substances if the culture of the microorganisms contains them in sufficient amounts.

As the orotic acid, purified preparations and any orotic acid-containing substances which do not inhibit the reaction, for example, .orotic acid fermentation broth of a microorganism or its partially purified product, can be used. Orotic acid is used at a concentration of 0.01 to 1.0 mol/l, preferably 0.01 to 0.3 mol/l. As the choline and/or phosphorylcholine, purified preparations and any substances containing choline and/or phosphorylcholine which do not inhibit the reaction can be used. The concentration of the choline and/or phosphorylcholine is within the range of 0.01 to 3.0 mol/l, preferably within the range of 0.02 to 1.0 mol/l.

As the energy donor, carbohydrates such as glucose, fructose and sucrose, molasses, starch hydrolysate, organic acids such as pyruvic acid, lactic acid, acetic acid and α-ketoglutaric acid, and amino acids such as glycine, alanine, aspartic acid and glutamic acid can be used. The energy donor is used at a concentration of 0.02 to 2.0 mol/l.

As the phosphate ion, orthophosphoric acid, pyrophosphoric acid, polyphosphoric acids such as tripolyphosphoric acid and tetrapolyphosphoric acid, polymetaphosphoric acids such as tetrapolymetaphosphoric acid, and inorganic phosphates such as potassium dihydrogenphosphate, dipotassium hydrogenphosphate, sodium dihydrogenphosphate and disodium hydrogenphosphate can be used. The phosphate ion is used at a concentration of 0.01 to 0.5 mol/l.

As the magnesium ion, inorganic magnesium salts such as magnesium sulfate, magnesium nitrate and magnesium chloride, and organic magnesium salts such as magnesium citrate can be used. The magnesium ion is usually added to the reaction mixture in an amount of 0.005 to 0.2 mol/l.

As the ammonium ion, aqueous ammonia, ammonia gas, various inorganic and organic ammonium salts, glutamine, yeast extract, Casamino acid, corn steep liquor, and other natural products containing glutamine can be used. The ammonium ion is usually added to the reaction mixture in an amount of 0.01 to 2.0 mol/l.

As the surfactant, any surfactant can be used so far as it promotes the production of CDP-choline. Examples of suitable surfactants include anionic surfactants such as sodium dioctyl sulfosuccinate (e.g. Rapisol manufactured by Nippon Oil and Fats Co., Ltd.) and lauroyl sarcosinate, nonionic surfactants such as polyoxyethylene cetyl ether (e.g. Nonion P-208 manufactured by Nippon Oil and Fats Co., Ltd.), and tert-amines such as alkyl dimethylamine (e.g. Tert-amine FB manufactured by Nippon. Oil and Fats Co., Ltd.). The surfactant is usually used at a concentration of 0.1 to 50 g/l, preferably 1 to 20 g/l.

As the organic solvent, xylene, toluene, aliphatic alcohols, acetone, ethyl acetate, etc. can be used. The organic solvent is usually used at a concentration of 0.1 to 50 ml/l, preferably 1 to 20 ml/l.

Recovery of the CDP-choline produced in the reaction mixture may be carried out in a conventional manner using activated carbon or anion exchange resin.

Certain embodiments of the present invention are illustrated in the following representative examples.

EXAMPLE 1

Construction of a recombinant plasmid for expressing CCT, CKI and pyrG simultaneously:

The method for the construction of a recombinant plasmid for expressing CCT, CKI and pyrG simultaneously is described below. The steps for the construction are shown in FIG. 1.

1) Expression of CCT/CKI Fused Protein

*E. coli* MM294/pCC41 strain carrying plasmid pCC41 containing the CCT gene derived from the yeast chromosome (hereinafter a plasmid-carrying strain is represented in the following manner: name of host strain/name of plasmid) was inoculated into 400 ml of L medium containing 10 g/l Bacto-tryptone (Difco Laboratories), 5 g/l yeast extract (Difco Laboratories) and 5 g/l sodium chloride, and adjusted to pH 7.2. Culturing was carried out at 30° C. for 18 hours. Plasmid pCC41 was isolated from the cultured cells by the known method mentioned above. Separately, plasmid pCK1D containing the CKI gene derived from the yeast chromosome was isolated from *E. coli* MM294/pCK1D strain in the same manner.

The obtained pCC41 plasmid DNA (5 μg) was dissolved in 50 μl of a buffer solution comprising 10 mM Tris-HCl (pH 7.5), 50 mM NaCl, 7 mM $MgCl_2$ and 6 mM 2-mercaptoethanol (hereinafter buffer solutions used for the digestion reaction with restriction enzymes are named, for example, "Y-50 buffer solution" according to the NaCl concentration). To the solution were added 20 units of Hind III (Takara Shuzo Co., Ltd.; hereinafter, all the restriction enzymes used were obtained from Takara Shuzo Co., Ltd.) and 20 units of Hpa I, and digestion reaction was carried out at 37° C. for 2 hours. The reaction mixture was subjected to agarose gel electrophoresis, and the larger DNA fragment of 3,808 bp was extracted from the gel and isolated. Separately, 5 μg of pCK1D plasmid DNA was digested with Hind III and Hpa I in the same manner, and a DNA fragment of 2,297 bp was isolated.

About 0.2 μg of the thus obtained DNA fragment derived from pCC41 and about 0.05 μg of the DNA fragment derived from pCK1D were subjected to ligation reaction with 2 units of T4 ligase (Takara Shuzo Co., Ltd.) in 40 μl of a buffer solution comprising 20 mM Tris-HCl (pH 7.6), 10 mM $MgCl_2$, 10 mM dithiothreitol and 0.5 mM ATP (hereinafter referred to as T4 ligase buffer) at 4° C. for 18 hours. The obtained recombinant DNA was used to transform *E. coli* MM294 strain, and a transformant resistant to ampicillin (50 μg/ml) was obtained.

A plasmid DNA was isolated from this transformant, and its structure was analyzed by digestion with restriction enzymes such as Hind III, Hpa I and Kpn I. As the result, it was confirmed that a plasmid of 6.1 kilobase pairs (hereinafter referred to as kb) having the desired structure was constructed. This plasmid was named pCK1 (see FIG. 1).

Figure 2:
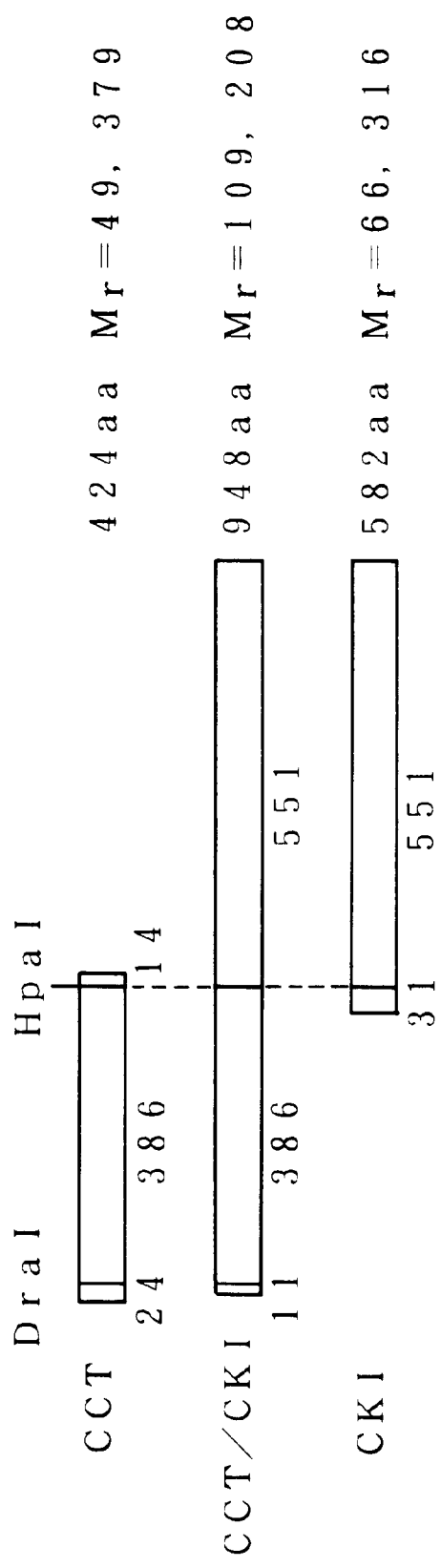
FIG. 2 illustrates the structure of CCT/CKI fused protein encoded by plasmid pCK1.
Figure 3:
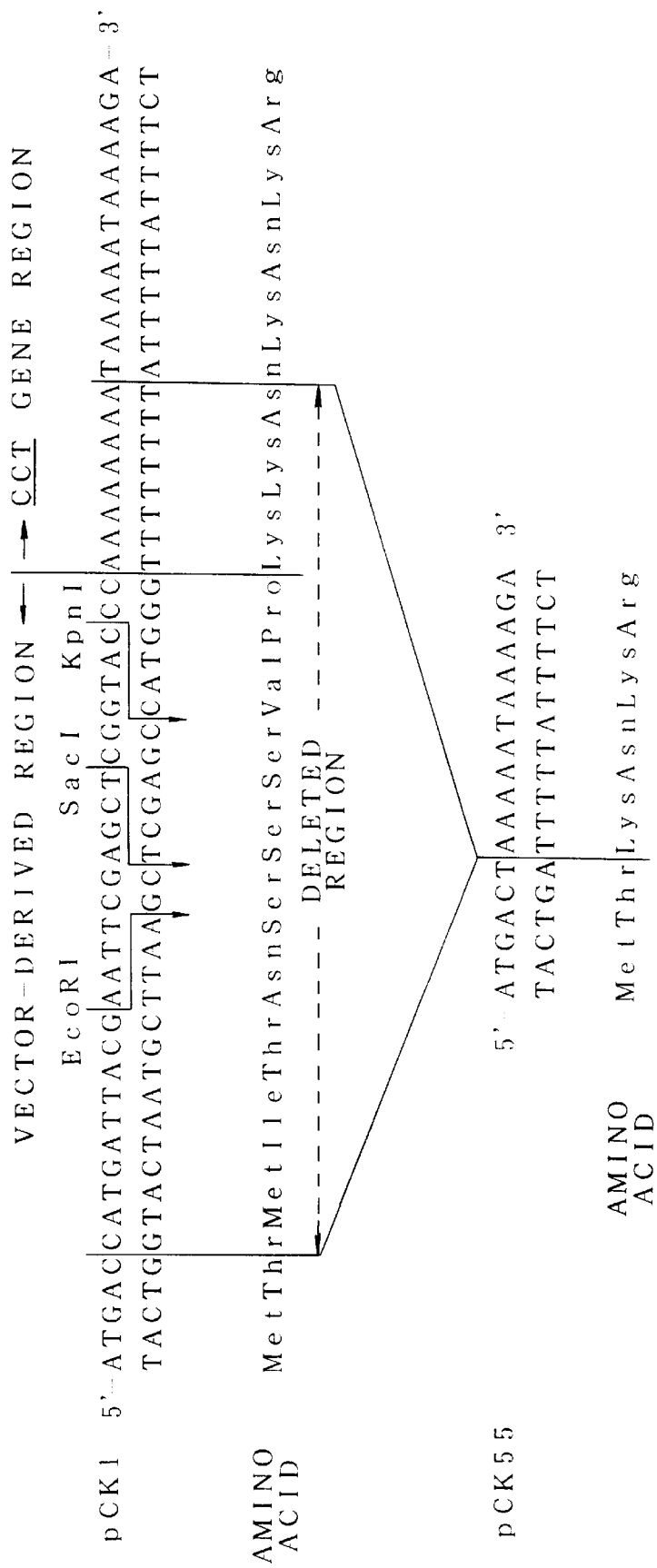
FIG. 3 shows the nucleotide sequence of the N-terminal region of the gene coding for CCT/CKI fused protein carried on plasmids pCK1 and pCK55. The nucleotide sequence and the corresponding amino acid sequence is represented by, SEQ ID NO:1 and SEQ ID NO:2. The nucleotide sequence and corresponding amino acid sequence after the deletion is removed is represented by SEQ ID NO:3 and SEQ ID NO:4.

FIG. 2 shows the structure of the CCT/CKI fused protein encoded by pCK1. pCC41 has the structure wherein the Dra I fragment of 1,296 bp derived from the yeast chromosome is inserted into E. coli vector pUC18 at the Sma I cleavage site of its multi-cloning sites. pCC41 comprises a DNA sequence wherein the region coding for 24 N-terminal amino acids was deleted from the DNA sequence of the CCT gene by the Dra I digestion and the sequence coding for 11 amino acids derived from the vector lacZ gene was attached instead (see FIG. 3). Plasmid pCK1 comprises, as a result of the Hpa I cleavage and ligation, the DNA sequence of the CCT gene further modified by the deletion of the region coding for 14 C-terminal amino acids and, ligated thereto, the DNA sequence wherein the region coding for 31 N-terminal amino acids was deleted from the DNA sequence of the CKI gene. Thus the fused protein encoded by pCK1 has the 948 amino acid sequence.

MM294/pCK1 strain was subjected to reaction according to the method for the determination of the CCT activity described below. The reaction in which CTP and phosphorylcholine were used as the substrates resulted in the formation of CDP-choline. The same result was obtained when 5 mM choline chloride was used instead of 5 mM phosphorylcholine, and 5 mM ATP was added. These results revealed that the pCK1-carrying strain had both CCT and CKI activities.

2) Preparation of CCT/CKI Fused Protein Lacking the N-Terminal Region

In order to increase the amount of the CCT/CKI fused protein produced by the expression of the gene, CCT/CKI fused protein lacking the N-terminal region was prepared according to the method described below.

In 30 $\mu$l of Y-50 buffer solution was dissolved 2 $\mu$g of pCK1 plasmid DNA, and 15 units of Kpn I was added to the solution. Digestion reaction was carried out at 37° C. for 2 hours. To the reaction mixture were added 20 $\mu$l of Bal 31 buffer solution [100 mM Tris-HCl (pH 8.0), 60 mM MgCl$_2$, 60 mM CaCl$_2$ and 3 M NaCl] at five-fold concentration, 46 $\mu$l of distilled water and 0.1 unit of Bal 31 nuclease (Takara Shuzo Co., Ltd.), and digestion reaction was carried out at 30° C. for 3 minutes.

Then, 100 $\mu$l of a phenol/chloroform mixture (volume ratio=1:1) was added to the reaction mixture, followed by adequate stirring to stop the reaction. The reaction mixture was subjected to centrifugation and the upper layer was separated. (The foregoing procedure is hereinafter referred to as phenol/chloroform extraction.) To the obtained aqueous layer was added a two-fold volume of ice-cooled ethanol, and the mixture was allowed to stand at −80° C. for 30 minutes, followed by centrifugation. The supernatant was discarded and the precipitate was dried under reduced pressure. (This procedure is hereinafter referred to as ethanol precipitation.) The supernatant was dissolved in 50 $\mu$l of T4 ligase buffer solution, and 1 unit of T4 ligase was added to the solution. The ligation reaction was carried out at 4° C. for 18 hours.

The thus obtained recombinant DNA was used to transform E. coli MM294 strain, and ampicillin-resistant transformants were selected and cultured. They were examined for CCT activity by the method described below, and the strain with the highest CCT activity was selected. A plasmid DNA was isolated from this transformant. By digestion with Hind III, Hpa I, Pvu II, etc. it was confirmed that the plasmid had the desired structure. The plasmid was named pCK55 (see FIG. 1).

The nucleotide sequence of the N-terminal region of the gene encoding the CCT/CKI fused protein on pCK55 was determined by the dideoxy method of F. Sanger at a. (J. Mol. Biol., 143, 161–178, 1980). As shown in FIG. 3, the gene codes for the fused protein which has the 936 amino acid sequence lacking the 12 amino acid sequence consisting of the 9 amino acid sequence derived from E. coli vector pUC18 and the 3 amino acid sequence derived from the CCT gene owing to the deletion of 36 bp sequence including the Kpn I cleavage site by the Bal 31 nuclease digestion.

3) Construction of a Plasmid for Expressing CCT, CKI and PyrG Simultaneously

A plasmid DNA was isolated from E. coli MM294/pMW6 strain carrying plasmid pMW6 containing the pyrG gene derived from the E. coli chromosome. pMW6 plasmid DNA (5 $\mu$g) was dissolved in 50 $\mu$l of Y-150 buffer, and 20 units of Mlu I was added to the solution. The digestion reaction was carried out at 37° C. for 2 hours. Then, phenol/chloroform extraction and ethanol precipitation were carried out, and the obtained DNA fragment was dissolved in 50 $\mu$l (total volume) of a DNA polymerase buffer solution comprising 50 mM Tris-HCl (pH 8.8), 7 mM MgCl$_2$, 6 mM 2-mercaptoethanol, 7 $\mu$M EDTA, 0.25 mM dATP, 0.25 mM dCTP, 0.25 mM dGTP and 0.25 mM dTTP, and 5 units of T4 DNA polymerase (Takara Shuzo Co., Ltd.) was added to the solution. The reaction was carried out at 37° C. for 2 hours, whereby the 5'-protruding end formed by the Mlu I digestion was changed to a blunt end. The reaction mixture was subjected to phenol/chloroform extraction and ethanol precipitation, and the resulting DNA fragment was dissolved in 50 $\mu$l of Y-50 buffer solution. To the solution was added 15 units of Hind III and digestion reaction was carried out at 37° C. for 2 hours. The digest was subjected to agarose gel electrophoresis, and the larger DNA fragment of 4,652 bp was extracted from the gel and isolated. Separately, plasmid pCK55 was isolated from MM294/pCK55 strain in the same manner. The obtained pCK55 plasmid DNA (5 $\mu$g) was dissolved in 50 $\mu$l of Y-50 buffer, and 20 units of Hind III and 20 units of Pvu II were added to the solution. Digestion reaction was carried out at 37° C. for 2 hours. The digest was subjected to agarose gel electrophoresis, and the larger DNA fragment of 3,610 bp containing the CCT/CKI gene was isolated. About 0.05 $\mu$g of the thus obtained DNA fragment derived from pMW6 and about 0.2 $\mu$g of the DNA fragment derived from pCK55 were subjected to ligation reaction with 2 units of T4 ligase in 50 $\mu$l of T4 ligase buffer at 40° C. for 18 hours. The obtained recombinant DNA was used to transform E. coli MM294 strain to give an ampicillin-resistant transformant.

A plasmid DNA was isolated from this transformant, and its structure was analyzed by digestion with restriction enzymes such as Hind III, Hpa I and Kpn I. As the result, it was confirmed that the desired plasmid of 8.3 kb was constructed. The plasmid was named pCKG55 (see FIG. 1).

4) CCT and PyrG Activities of the Strains Carrying Recombinant DNAS

The CCT and pyrG activities of the strains carrying recombinant DNAs were determined in the following manner.

Each of the E. coli strains to be examined was inoculated into 10 ml of L medium containing 50 $\mu$l/ml ampicillin in a large test tube, and cultured at 25° C. for 18 hours with shaking. The resulting seed culture (100 $\mu$l) was inoculated into 10 ml of L medium containing 50 $\mu$l/ml ampicillin in a large test tube and cultured at 33° C. for 10 hours with shaking. The culture (500 μl) was subjected to centrifugation and the supernatant was discarded. The obtained cells were suspended in 500 μl of a 20 mM potassium phosphate buffer (pH 7.0), followed by addition of 5 μl of xylene. The mixture was stirred at 30° C. for 10 minutes. The thus obtained xylene-treated product was used as a crude enzyme solution whose enzymatic activity was determined in the following manner.

Determination of CCT Activity

A mixture (500 μl) comprising a 150 mM potassium phosphate buffer solution (pH 7.5), 25 mM magnesium chloride, 5 mM CTP, 5 mM phosphorylcholine and the crude enzyme solution was subjected to reaction at 30° C. for 2 hours. The reaction mixture was intermittently taken in 50 μl portions, and 50 μl of 0.2 M acetic acid was added, followed by heating at 100° C. for 2 minutes to stop the reaction. The obtained product was centrifuged, and the supernatant was appropriately diluted with distilled water. The amount of CDP-choline produced was determined by high performance liquid chromatography. The enzyme activity was indicated as unit (U) per ml culture, one unit being defined as the amount of the enzyme which catalyzes the formation of 1 μmol of CDP-choline in one minute.

Determination of PyrG Activity

A mixture (2 ml) comprising 40 mM Tris-HCl (pH 7.1), 10 mM magnesium chloride, 1 mM ATP, 1 mM UTP, 0.2 mM GTP, 2 mM glutamine, 8 mM phosphoenolpyruvic acid and the crude enzyme solution was subjected to reaction at 38° C. for 60 minutes. The reaction mixture was intermittently taken in 200 μl portions, and 1.8 ml of 3.5% perchloric acid was added to stop the reaction.

This acid-treated reaction mixture was centrifuged, and the absorbance of the supernatant at 291 nm was measured using a calorimeter. In the 3.5% perchloric acid, little absorption of light is observed for the substrate UTP at 291 nm, whereas the product CTP shows absorption of light. Thus, the measurement of the absorbance at 291 nm provides data on the quantity of the CTP produced. The enzyme activity was indicated as unit (U) per ml culture, one unit being defined as the amount of the enzyme which catalyzes the formation of 1 μmol of CTP in one minute.

Table 1 shows the results of the determination of the CCT and pyrG activities of the strains which carry the plasmids constructed according to the present invention.

The pCKG55-carrying $E.$ $coli$ MM294 strain, $Escherichia$ $coli$ MM294/pCKG55 was deposited with the Fermentation Research Institute, Agency of Industrial Science and Technology, on Jan. 27, 1992 under the Budapest Treaty with the accession number of FERM BP-3717.

TABLE 1

| Host strain | Plasmid | CCT activity (U/ml) | pyrG activity (U/ml) |
|---|---|---|---|
| MM294 | pCC41 | 0.052 | 0 |
| MM294 | pMW6 | 0 | 0.27 |
| MM294 | pCK1 | 0.035 | 0 |
| MM294 | pCK55 | 0.053 | 0 |
| MM294 | pCKG55 | 0.048 | 0.21 |

EXAMPLE 2

$E.$ $coli$ MM294/pCKG55 strain obtained in Example 1 was inoculated into 10 ml of L medium containing 50 μg/ml ampicillin in a large test tube, and cultured with shaking at 300 rpm at 25° C. for 24 hours. The resulting culture (20 ml) was inoculated into 400 ml of L medium containing 50 μg/ml ampicillin in a 2-l Erlenmeyer flask with baffles, and cultured with rotary shaking at 190 rpm at 25° C. for 16 hours.

The culture (125 ml) was transferred to a 5-l jar fermentor containing 2.5 l of a liquid medium (no pH adjustment) comprising 5 g/l glucose (separately sterilized), 5 g/l peptone (Kyokuto Seiyaku Kogyo Co., Ltd.), 6 g/l $Na_2HPO_4$, 3 g/l $KH_2PO_4$, 5 g/l NaCl, 1 g/l $NH_4Cl$, 250 mg/l $MgSO_4.7H_2O$ (separately sterilized), and 4 mg/l vitamin B1 (separately sterilized). Culturing was carried out at 25° C. for 11 hours, and then at 32° C. for 13 hours, with stirring (600 rpm) and aeration (2.5 l/min.). During the culturing, the pH was adjusted to 7.0 with 14% aqueous ammonia. Addition of a feed solution composed of 167 g/l glucose and 167 g/l peptone to the culture using a Perista pump was started 11 hours after the start of culturing and was continued for 13 hours at a rate of 30 ml per hour.

On the other hand, $Corynebacterium$ $ammoniagenes$ ATCC 21170 was inoculated into 10 ml of a liquid medium in a large test tube, the medium comprising 50 g/l glucose, 10 g/l polypeptone (Daigo Eiyo Kagaku Co., Ltd.), 10 g/l yeast extract (Daigo Eiyo Kagaku Co., Ltd.), 5 g/l urea, 5 g/l $(NH_4)_2SO_4$, 1 g/l $KH_2PO_4$, 3 g/l $K_2HPO_4$, 1 g/l $MgSO_4.7H_2O$, 0.1 g/l $CaCl_2.2H_2O$, 10 mg/l $FeSO_4.7H_2O$, 10 mg/l $ZnSO_4.7H_2O$, 20 mg/l $MnSO_4.4–6H_2O$, 20 mg/l L-cysteine, 10 mg/l calcium D-pantothenate, 5 mg/l vitamin B1, 5 mg/l nicotinic acid, and 30 μg/l biotin, and being adjusted to pH 7.2 with sodium hydroxide. Reciprocative shaking culture was carried out at 300 rpm at 28° C. for 24 hours.

The resulting culture (20 ml) was inoculated into 230 ml of a liquid medium having the same composition as mentioned above in a 2-l Erlenmeyer flask with baffles, and cultured with rotary shaking at 190 rpm at 28° C. for 24 hours.

The culture (250 ml) was then inoculated into 2.5 l of a liquid medium in a 5-l jar fermentor, the medium comprising 100 g/l glucose, 10 g/l meat extract, 10 g/l polypeptone, 1 g/l $KH_2PO_4$, 1 g/l $K_2HPO_4$, 1 g/l $MgSO_4.7H_2O$, 0.1 g/l $CaCl_2.2H_2O$, 20 mg/l $FeSO_4.7H_2O$, 10 mg/l $ZnSO_4.7H_2O$, 20 mg/l $MnSO_4.4–6H_2O$, 15 mg/l β-alanine, 20 mg/l L-cysteine, 100 μg/l biotin, 2 g/l urea (separately sterilized), and 5 μg/l vitamin B1 (separately sterilized), and being adjusted to pH 7.2 with sodium hydroxide. Seed culturing was carried out at 32° C. with stirring (600 rpm) and aeration (2.5 l/min.). During the culturing, the pH was adjusted to 6.8 with concentrated aqueous ammonia.

When the glucose in the supernatant of the above seed culture was completely consumed, a 350 ml portion of the culture was harvested aseptically, and inoculated into 2.5 l of a liquid medium in a 5-l jar fermentor, the medium comprising 180 g/l glucose, 10 g/l $KH_2PO_4$, 10 g/l $K_2HPO_4$, 10 g/l $MgSO_4.7H_2O$, 0.1 g/l $CaCl_2.2H_2O$, 20 mg/l $FeSO_4.7H_2O$, 10 mg/l $ZnSO_4.7H_2O$, 20 mg/l $MnSO_4.4–6H_2O$ (separately sterilized), 15 mg/l β-alanine, 20 mg/l L-cysteine, 1 g/l sodium glutamate, 100 μg/l biotin, 2 g/l urea (separately sterilized), and 5 mg/l vitamin B1 (separately sterilized), and being adjusted to pH 7.2 with sodium hydroxide. The main culturing was carried out at 32° C. with stirring (600 rpm) and aeration (2.5 l/min.). During the culturing, the pH was adjusted to 6.8 with concentrated aqueous ammonia. The culturing was terminated when the glucose in the supernatant of the culture was completely consumed.

Then, 360 ml of the culture of $E.$ $coli$ MM294/pCKG55 and 360 ml of the culture of $Corynebacterium$ $ammoni-$ agenes ATCC 21170 were poured into a 2-l jar fermentor, to which 100 g/l glucose, 10 g/l (47 mM) orotic acid, 8.4 g/l (60 mM) choline chloride, 5 g/l $MgSO_4 \cdot 7H_2O$, and 20 ml/l xylene were added, followed by addition of distilled water to make a total volume of 800 ml. The mixture was subjected to reaction at 32° C. with stirring (800 rpm) and aeration (0.8 l/min.). During the reaction, the pH was adjusted to 7.2 with 10N sodium hydroxide, and $KH_2PO_4$ was added appropriately so that the $KH_2PO_4$ concentration of the supernatant of the reaction mixture could be kept at 1 to 5 g/l. By the reaction for 23 hours, 11.0 g/l (21.5 mM) CDP-choline was produced. In contrast, no CDP-choline was produced in the reaction in which 360 ml of distilled water was used instead of the culture of *E. coli* MM294/pCKG55. When 360 ml of distilled water was used in place of the culture of *Corynebacterium ammoniagenes* ATCC 21170, the quantity of CDP-choline produced was 0.7 g/l (1.4 mM).

EXAMPLE 3

The reaction was carried out in the same manner as in Example 2 except that 16.5 g/l (50 mM) phosphorylcholine was used as the substrate instead of choline chloride. By the reaction for 23 hours, 9.5 g/l (18.6 mM) CDP-choline was produced.

What is claimed is:

1. A process for producing cytidine diphosphate choline, which comprises contacting an enzymatically active treatment product of a culture of a microorganism which carries a recombinant DNA comprising a DNA fragment encoding pyrG, CCT and CKI and a vector (hereinafter referred to as Microorganism A1) and an enzymatically active treatment product of a culture of another microorganism which has orotate phosphoribosyltransferase, OMP decarboxylase, nucleosidemonophosphate kinase and nucleosidesiphosphate kinase activities (hereinafter referred to as Microorganism B) with orotic acid and choline in a liquid medium; allowing cytidine diphosphate choline to accumulate in the liquid medium; and recovering cytidine diphosphate choline from the liquid medium.

2. A process for producing cytidine diphosphate choline, which comprises contacting an enzymatically active treatment product of a culture of a microorganism which carries a recombinant DNA comprising a DNA fragment encoding pyrG and CCT and a vector (hereinafter referred to as Microorganism A2) and an enzymatically active treatment product of a culture of another microorganism which as orotate phosphoribosyltransferase, OMP decarboxylase, nucleosidemonophosphate kinase and nucleosidediphosphate kinase activities (hereinafter referred to as Microorganism B) with orotic acid and phosphorylcholine in a liquid medium; allowing cytidine diphosphate choline to accumulate in the liquid medium; and recovering cytidine diphosphate choline from the liquid medium.

3. A process according to claim 1, wherein the DNA encoding CCT and CKI are derived from *Saccharomyces cerevisiae*, and the DNA encoding pyrG is derived from *Escherichia coli*.

4. A process according to claim 1, wherein Microorganism A1 is a microorganism belonging to the genus Escherichia and Microorganism B is a microorganism belonging to the genus Corynebacterium.

5. A process according to claim 1, wherein Microorganism A1 is *Escherichia coli* MM294/pCKG55 (FERM BP-3717).

6. A process according to claim 1, wherein Microorganism B is *Corynebacterium ammoniagenes* ATCC 21170.

7. A process according to claim 2, wherein the DNA encoding CCT is derived from *Saccharomyces cerevisiae*, and the DNA encoding pyrG is derived from *Escherichia coli*.

8. A process according to claim 2, wherein Microorganism A2 is a microorganism belonging to the genus Escherichia and Microorganism B is a microorganism belonging to the genus Corynebacterium.

9. A process according to claim 2, wherein Microorganism B is *Corynebacterium ammoniagenes* ATCC 21170.

* * * * *

UNITED STATES PATENT AND TRADEMARK OFFICE
CERTIFICATE OF CORRECTION

PATENT NO. : 6,387,667 B1　　　　　　　　　　　　　　　　　　　　　　　Page 1 of 1
DATED : May 14, 2002
INVENTOR(S) : Maruyama et al.

It is certified that error appears in the above-identified patent and that said Letters Patent is hereby corrected as shown below:

Column 13,
Line 56, "as" should be -- has --.

Column 14,
Lines 42-43, "Escherichia" should be -- *Escherichia* --.
Line 44, "Corynebacterium" should be -- *Corynebacterium* --.
Lines 55-56, "Escherichia" should be -- *Escherichia* --.
Line 57, "Corynebacterium" should be -- *Corynebacterium* --.

Signed and Sealed this

Twenty-fifth Day of February, 2003

JAMES E. ROGAN
*Director of the United States Patent and Trademark Office*